United States Patent
Shah et al.

(10) Patent No.: US 9,393,279 B2
(45) Date of Patent: *Jul. 19, 2016

(54) ENTERIC COATED MULTIPARTICULATE CONTROLLED RELEASE PEPPERMINT OIL COMPOSITION AND RELATED METHODS

(71) Applicant: Zx Pharma, LLC, Boca Raton, FL (US)

(72) Inventors: Syed M. Shah, Boca Raton, FL (US); Daniel Hassan, Boca Raton, FL (US); Fred Hassan, Boca Raton, FL (US)

(73) Assignee: Zx Pharma, LLC, Boca Raton, FL (US)

( * ) Notice: Subject to any disclaimer, the term of this patent is extended or adjusted under 35 U.S.C. 154(b) by 0 days.

This patent is subject to a terminal disclaimer.

(21) Appl. No.: 14/461,687

(22) Filed: Aug. 18, 2014

(65) Prior Publication Data

US 2014/0356440 A1 Dec. 4, 2014

Related U.S. Application Data

(63) Continuation of application No. 14/033,761, filed on Sep. 23, 2013, now Pat. No. 8,808,736, which is a continuation-in-part of application No. 13/367,747, filed on Feb. 7, 2012, now Pat. No. 8,568,776.

(60) Provisional application No. 61/880,294, filed on Sep. 20, 2013, provisional application No. 61/815,073, filed on Apr. 23, 2013, provisional application No. 61/486,523, filed on May 16, 2011, provisional application No. 61/441,716, filed on Feb. 11, 2011.

(51) Int. Cl.
| | |
|---|---|
| *A61K 9/50* | (2006.01) |
| *A61K 36/534* | (2006.01) |
| *A61K 9/16* | (2006.01) |
| *A61K 47/38* | (2006.01) |

(52) U.S. Cl.
CPC ............. *A61K 36/534* (2013.01); *A61K 9/1658* (2013.01); *A61K 9/1682* (2013.01); *A61K 9/5026* (2013.01); *A61K 9/5057* (2013.01); *A61K 9/5073* (2013.01); *A61K 47/38* (2013.01); *A61K 9/5042* (2013.01)

(58) Field of Classification Search
CPC .... A61K 9/5057; A61K 9/5042; A61K 47/38
See application file for complete search history.

(56) References Cited

U.S. PATENT DOCUMENTS

| | | | |
|---|---|---|---|
| 3,515,781 A | 6/1970 | Steinberg | |
| 4,687,667 A | 8/1987 | Rhodes et al. | |
| 4,786,505 A | 11/1988 | Lovgren et al. | |
| 5,362,745 A | 11/1994 | Graziella | |
| 5,397,573 A * | 3/1995 | Kajs et al. ..................... | 424/451 |
| 5,418,010 A | 5/1995 | Janda et al. | |
| 5,498,423 A | 3/1996 | Zisapel | |
| 5,688,510 A | 11/1997 | Nakamichi et al. | |
| 5,840,332 A | 11/1998 | Lerner et al. | |
| 6,139,877 A | 10/2000 | Debregeas et al. | |
| 6,306,435 B1 | 10/2001 | Chen et al. | |
| 6,365,185 B1 | 4/2002 | Ritschel et al. | |
| 6,423,349 B1 | 7/2002 | Sherratt et al. | |
| 6,531,152 B1 | 3/2003 | Lerner et al. | |
| 6,632,451 B2 | 10/2003 | Penhasi et al. | |
| 6,726,927 B2 | 4/2004 | Chen | |
| 6,972,132 B1 | 12/2005 | Kudo et al. | |
| 7,041,316 B2 | 5/2006 | Chen | |
| 7,048,945 B2 | 5/2006 | Percel et al. | |
| 7,115,282 B2 | 10/2006 | Shefer et al. | |
| 7,670,619 B2 | 3/2010 | Mihaylov | |
| 7,670,624 B2 | 3/2010 | Tsutsumi et al. | |
| 7,790,215 B2 | 9/2010 | Sackler et al. | |
| 7,790,755 B2 | 9/2010 | Akiyama et al. | |
| 7,803,817 B2 | 9/2010 | Kostadinov et al. | |
| 7,829,122 B2 | 11/2010 | Bruna et al. | |
| 7,838,027 B2 | 11/2010 | Rao et al. | |
| 8,337,811 B1 | 12/2012 | Sung et al. | |
| 8,361,439 B1 | 1/2013 | Sung et al. | |
| 8,524,257 B2 | 9/2013 | Nowak et al. | |
| 8,535,640 B1 | 9/2013 | Sung et al. | |
| 8,545,880 B2 | 10/2013 | Li et al. | |
| 8,568,776 B2 * | 10/2013 | Shah .................... | A61K 9/5026 424/468 |
| 8,574,544 B1 | 11/2013 | Sung et al. | |
| 8,808,736 B2 * | 8/2014 | Shah .................... | A61K 9/5073 424/458 |
| 2001/0038863 A1 | 11/2001 | Jaenicke | |
| 2002/0114832 A1 | 8/2002 | Herrmann et al. | |
| 2002/0192285 A1 | 12/2002 | Mulye | |
| 2003/0040539 A1 | 2/2003 | Zisapel | |

(Continued)

FOREIGN PATENT DOCUMENTS

| | | |
|---|---|---|
| CN | 1886119 B | 4/2015 |
| EP | 0015334 B1 | 5/1982 |

(Continued)

OTHER PUBLICATIONS

ISR for PCT/US12/41226, Issued Aug. 16, 2012.
Kim et al. (The Influence of Surelease and Sodium Alginate on the In-Vitro Release of Tamsulosin Hydrochloride in Pellet Dosage Form., J Pharm Pharmacol, Jun. 2005; 57(6): 735-42.
Office Action for U.S. Appl. No. 14/524,326, Issued Apr. 23, 2015.
Alexander Ford, Nicholas J. Talley, Brennan M Spiegel, Amy E Foxx-Orenstein, Lawrence Schiller, Eamonn M Quigley, Paul Moayyedi; Effect of Fibre, Antispasmodics, and Peppermint Oil in the Treatment of Irritable Bowel Syndrome: Systematic Review and Meta-Analysis; BMJ Research; Sep. 24, 2008.

(Continued)

*Primary Examiner* — Ali Soroush
(74) *Attorney, Agent, or Firm* — Christopher M. Ramsey; GrayRobinson, P.A.

(57) ABSTRACT

A multiparticulate composition is formed from a plurality of individual cores including a hydrophobic phase containing peppermint oil dispersed in a microcrystalline cellulose-based gel and a hydrophilic phase containing a hydrogel. An enteric coating is over the individual cores. The multiparticulate composition can be used to treat gastrointestinal disorders.

33 Claims, 2 Drawing Sheets

(56) References Cited

U.S. PATENT DOCUMENTS

| | | |
|---|---|---|
| 2003/0143272 A1 | 7/2003 | Waterman |
| 2003/0207851 A1 | 11/2003 | Wei |
| 2004/0052846 A1 | 3/2004 | Prater et al. |
| 2004/0062778 A1 | 4/2004 | Shefer et al. |
| 2005/0069579 A1 | 3/2005 | Kamaguchi et al. |
| 2005/0129761 A1* | 6/2005 | Venkata Ramana Rao et al. ............... 424/470 |
| 2005/0164987 A1 | 7/2005 | Barberich |
| 2005/0169987 A1 | 8/2005 | Korber |
| 2005/0181047 A1 | 8/2005 | Romero |
| 2005/0202079 A1 | 9/2005 | Bielski et al. |
| 2005/0281876 A1 | 12/2005 | Li et al. |
| 2006/0009465 A1 | 1/2006 | Edgar et al. |
| 2006/0127489 A1 | 6/2006 | Crothers et al. |
| 2006/0210631 A1 | 9/2006 | Patel et al. |
| 2006/0246134 A1 | 11/2006 | Venkatesh |
| 2006/0257469 A1 | 11/2006 | Bulka |
| 2006/0280795 A1 | 12/2006 | Penhasi et al. |
| 2007/0231388 A1 | 10/2007 | Anstett-Klein et al. |
| 2007/0292510 A1 | 12/2007 | Huang |
| 2008/0139510 A1 | 6/2008 | Rose |
| 2008/0152719 A1 | 6/2008 | Petereit et al. |
| 2008/0166416 A1 | 7/2008 | Lizio et al. |
| 2008/0199518 A1 | 8/2008 | Ku et al. |
| 2008/0299199 A1 | 12/2008 | Bar-Shalom |
| 2009/0004262 A1 | 1/2009 | Shaw et al. |
| 2009/0004281 A1 | 1/2009 | Nghiem et al. |
| 2009/0137670 A1 | 5/2009 | Kramer et al. |
| 2009/0227670 A1 | 9/2009 | Berg |
| 2009/0238905 A1 | 9/2009 | Gurney et al. |
| 2009/0246301 A1 | 10/2009 | Ehrenpreis et al. |
| 2010/0119601 A1 | 5/2010 | McCarty |
| 2010/0183713 A1 | 7/2010 | Tsutsumi et al. |
| 2010/0203134 A1 | 8/2010 | Chenevier et al. |
| 2010/0298379 A1 | 11/2010 | Jacobsen |
| 2011/0053866 A1 | 3/2011 | Duffield et al. |
| 2011/0064830 A1 | 3/2011 | Muller et al. |
| 2011/0081451 A1 | 4/2011 | Siegel et al. |
| 2012/0207842 A1 | 8/2012 | Shah et al. |
| 2012/0277323 A1 | 11/2012 | Kumar et al. |
| 2012/0301541 A1 | 11/2012 | Haronsky et al. |
| 2012/0301546 A1 | 11/2012 | Hassan |
| 2013/0230597 A1 | 9/2013 | Cook et al. |
| 2014/0178468 A1 | 6/2014 | Shear et al. |

FOREIGN PATENT DOCUMENTS

| | | |
|---|---|---|
| EP | 1953625 A | 8/2008 |
| EP | 1958625 A1 | 8/2008 |
| JP | 2000247870 | 9/2000 |
| JP | 2007197378 | 8/2007 |
| JP | 2008127349 | 6/2008 |
| JP | 2010189443 | 9/2010 |
| JP | 5201819 | 6/2013 |
| JP | 2015024986 | 2/2015 |
| WO | 9513794 | 5/1995 |
| WO | 9959544 | 11/1999 |
| WO | 2005027878 A | 3/2005 |
| WO | 2005032513 A2 | 4/2005 |
| WO | 2006097427 A1 | 9/2006 |
| WO | 2007012856 A | 2/2007 |
| WO | 2008057802 A | 5/2008 |
| WO | 2008134807 A | 11/2008 |
| WO | 2009077749 A | 6/2009 |
| WO | 2010144943 A | 12/2010 |
| WO | 2012109216 A | 8/2012 |
| WO | 2012170488 A | 12/2012 |
| WO | 2012170611 A | 12/2012 |
| WO | 2014065390 A1 | 5/2014 |

OTHER PUBLICATIONS

Singh, Saranjit; Rao, KV. Rama; Venugopal, Rao, K.; Manikandan, R.; "Alteration in Dissolution Characteristics of Gelatin-Containing Formulations"; Pharmaceutical Technology, Apr. 2002.

Abdul et al., A Flexible Technology of Modified-Rlease Drugs: Multiple-Unite Pellet System (MUPS), J Controlled Release 147: 2-16 (2010).

Chourasia et al., Pharmaceutical Approaches to Colon Targeted Drug Delivery Systems, J Pharm Pharmaceut Sci 6: 33-66 (2003).

Office Action for U.S. Appl. No. 14/064,685 issued Sep. 24, 2014.

Baranuskiene et al., Flavor Retention of Peppermint (*Mentha piperita* I.) Essential Oil Spray-Dried ni Modified Starches during Encapsulation and Storage, J. Agric. Food Chem., 2007, 55, 3027-3036.

Benes et al., Transmucosal, Oral Controlled-Release and Transdermal Drug Administration in Human Subjects: A Corssover Study with Melatonin, Journal of Pharmaceutical Sciences / 1115, vol. 86, No. 10, Oct. 1997.

Bogentoft et al., Influence of Food on the Absorption of Acetylsalicylic Acid From Enteric-Coated Dosage Forms, European J. Clin. Pharmacol., 14, 351-355, 1978.

Cellulose acetate phthalate enter coating (enerexusa.com/articles/enteric_coating.htm., last visit Feb. 6, 2014).

Clark et al., Variations in Composition of Peppermint Oil in Relation to Production Areas, Economic Botany 35(1), 1981, pp. 59-69, Bronx, NY, USA.

Committee for Proprietary Medicinal Products, Note for Guidance on Quality of Modified Release Products: A: Oral Dosage Forms, B: Transdermal Dosage Forms, Jul. 29, 1999, The European Agency for the Evaluation of Medicinal Products, London.

Dey et al., Multiparticulate Drug Deliver Systems for Controlled Release, Tropical Journal of Pharmaceutical Research, Sep. 2008; 7(3): 1067-1075, Pharmacotherapy Group, Faculty of Pharmacy, University of Benin, Benin City, 300001 Nigeria.

Digenis, Geroge A., The in vivo behavior of multiparticulate versus single unit dose formulations, presented at Capsugel's Symposium in Seoul (Apr. 10, 1990) and Tokyo (Apr. 12, 1990).

Dong et al., Effect of processing parameters on the formation of spherical multinuclear microcapsules encapsulating peppermint oil by coacervation, Journal of Microencapsulation, Nov. 2007; 24(7): 634-646.

Faroongsarng et al., The Swelling & Water Uptake of Tablets III: Moisture Sorption Behavior of Tablet Disintegrants, Drug Development and Industrial Pharmacy, 20(5), 779-798, (1994).

Final Report on the Safety Assessment of Mentha Piperita (Peppermint) Oil, Mentha Piperita (Peppermint) Leaf Extract, Mentha Piperita (Peppermint) Leaf, and Mentha Piperita (Peppermint) Leaf Water, International Journal of Toxicology, 2001 20:61, online version at http://ijt.sagepub.com/content/20/3/_suppl/61.

Galeotti et al., Menthol: a natural analgesic compound, Neuroscience Letters 322 (2002), pp. 145-148, Florence, Italy.

Grigoleit et al., Gastrointestinal clinical pharmacology of peppermint oil, Phytomedicine 12, (2005), pp. 607-611, Wiesbaden, Germany.

International Search Report of Feb. 16, 2014 for PCT/US2013/061141.

International Search Report of Feb. 4, 2014 for PCT/US2013/061146.

International Search Report of Jan. 29, 2014 for PCT/US2013/000217.

International Search Report of PCT/US2012/024110.

Juergens, et al., The Anti-Inflammatory Activity of L-Menthol Compared to Mint Oil in Human Monocytes In Vitro: A Novel Perspective for Its Therapeutic Use in Inflammatory Diseases, Eur J. Med Res (1998) 3: 539-545, Dec. 16, 1998.

Kellow et al., Altered Small Bowel Motility in Irritable Bowel Syndrome is Corrected With Symptoms, Gastroenterology, 1987, vol. 92, pp. 1885-1893, Rochester, Minnesota, USA.

Kline et al., Enteric-Coated pH-dependent peppermint oil capsules for the treatment of irritable bowel syndrome in children, J Pediatr 2001; 138: 125-8.

Kline, et al., Enteric-coated, pH-dependent peppermint oil capsules for the treatment of irritable bowel syndrome in children, J Pediatr 2001; 138: 125-8.

Lee et al, Design and evaluationof an oral controlled release delivery systme for melatonin in humans subjects, International Journal of Pharmaceutics 124 (1995) 119-127, College of Pharmacy, Kangwon National University, Chuncheon, South Korea, Department of

(56) References Cited

OTHER PUBLICATIONS

Pharmaceutics, College of pHarmacy, Oregeon State University, Corvallis, OR 97331-3507, USA, Department of Psychiatry, School of Medicine, Oregon Health Sciences University, Portland, OR, USA.

Lee et al., Formulation and Release Characteristics of Hydroxpropyl Methycellulose Matrix Tablet Containing Melatonin, Drug Development and Industrial Pharmacy, 25(4), 493-501 (1999), Biological Rhythm and Controlled Release Laboratory, College of Pharmacy, Kangwon National University, Chuncheon 200-709, Korea.

Liu et al., pH-resonsive amphiphilic hydrogel networks with IPN structure; A strategy for controlled drug release, International Journal of Pharmaceutics 308 (2006) 205-209, Department of Applied Chemistry, School of Science, Northwestern Polytechnic University, Xi'an 710072, PR China.

MacPherson et al., More than cool: promiscuous relationships of menthol and other sensory compounds, Mol. Cell. Neurosci, vol. 32, 2006, pp. 335-343.

McIntyre et al., Melatonin Rhythm in Human Plasma and Saliva, Journal of Pineal Research 4:177-183 (1987), Psychoendocrine Research Unit, Department of Psychiatry, Austin Hospital Heidelbert (I.M.M., T.R.N., G.D.B.), and Department of Psychology, Brain Behaviour Research Institute, Latrobe University, Bundoora (S.M. A.), Victoria, Australia.

Menthols (inchem.org/documents/sids/sids/MENTHOLS.pdf, lat visit Feb. 6, 2014).

Micklefield, et al., Effects of Peppermint Oil and Caraway Oil on Gastroduodenal Motility, Phytother. Res. 14, 20-23 (2000).

Office Action for U.S. Appl. No. 14/033,713 issued May 14, 2014.
Office Action for U.S. Appl. No. 14/033,737 issued Apr. 23, 2014.
Office Action for U.S. Appl. No. 14/064,685 issued Mar. 7, 2014.

Pilbrant et al., Development of an oral formulation of omeprazole, Scand J. Gastroenterol, 1985, vol. 20 (suppl. 108, pp. 113-120, Molndal, Sweden.

Pittler et al., Peppermint Oil for Irritable Syndrome: A Critical Review and Metaanalysis, The American Journal of Gastroenterology, vol. 93, No. 7, 1998, 1131-1135.

Rees et al., Treating irritable bowel syndrome with peppermint oil, British Medical Journal, Oct. 6, 1979.

Rohloff et al., Effect of Harvest Time and Drying Method of Biomass Production, Essential Oil Yield, and Quality of Peppermint (*Mentha x piperita* L.), J. Agric. Food Chem., 2005, vol. 53, pp. 4143-4148 Hedmark, Norway.

RXMED: Pharmaceutical Information—Colpermin, Peppermint Oil Symptomatic Relief of Irritable Bowel Syndrome, Jan. 4, 2010.

Sibanda et al., Experimental Design for the Formulation and Optimization of Novel Cross-Linked Oilspheres Developed for In Vitro Site-Specific Release of Mentha piperita Oil, AAPS PharmSciTech 2004; 5(1) Article 18 (http://www.aapsharmscitech.org, submitted Nov. 5, 2003, Accepted Feb. 18, 2004.

Somerville et al., Delayed release peppermint oil capsules (Colpermin) for the spastic colon syndrome: a pharmacokinetic study, Br. J. clin. Pharmac., (1984), vol. 18, pp. 638-640, Ipswich, United Kingdom.

Stevens et al., The short term natural history of irritable bowel syndrome: a time series analysis, Behav. Res. Ther., vol. 35, No. 4, pp. 319-326, 1997, Albany, NY, USA.

Thomposon, Shaun, List of Proton Pump Inhibitors, Mar. 12, 2011, http://www.livestrong.com/article/26705-list-proton-pump-inhibitors.

Tran et al., New findings on melatonin absorption and alterations by pharmaceutical excipients using the Ussing chamber technique with mounted rat gastrointestinal segments, International Journal of Pharmaceuticals 378 (2009) pp. 9-16, Bioavailability Control Laboratory, College Pharmacy, Kangwon National University, Chuncheon 200-701, Republic of Korea.

Trimble et al., Heightened Visceral Sensation in Functional Gastrointestinal Disease Is Not Site-Specific, Digestive Diseases and Sciences, vol. 40, No. 8, Aug. 1995, pp. 1607-1613.

White et al., A pharmacokinetic comparison of two delayed-release peppermint oil preparations, Colpermin and Mintec, for treatment of the irritable bowel syndrome, International Journal of Pharmaceutics, 40, (1987), pp. 151-155.

Yuasa et al., Whisker Growth of I-menthol in coexistence with various excipents, International Journal of Pharmacutics 203, (2000), pp. 203-210, Tokyo, Japan.

Bigi, A., Cojazzi, S. Panzavolta, K., Rubini, N., Roved, N., "Mechanical and Thermal Properties of Gelatin Films at Different Degrees of Glutaraldehyde Crosslinking": Biometerials 22; 2001; pp. 764-768.

Eccles, "Menthol: Effects On Nasal Sensation Of Airflow And The Drive To Breath", Rhinitis, Common Cold and Nasal Research Centre, Cardiff School of Biosciences; pp. 210-214; 2003.

Hawthorne, M; The Actions of Peppermint Oil and Menthol on Calcium Channel Dependent Processes in Intestinal, Neuronal and Cardiac Preparations; Department of Biochemical Pharmacology, State University of New York; Oct. 14, 1987.

Office Action for U.S. Appl. No. 14/524,648 issued Mar. 24, 2016.
Office Action for U.S. Appl. No. 14/876,465 issued Jan. 25, 2016.
Office Action for U.S. Appl. No. 14/918,042 issued Jan. 8, 2016.

* cited by examiner

ENTERIC COATED MULTIPARTICULATE CONTROLLED RELEASE PEPPERMINT OIL COMPOSITION AND RELATED METHODS

CROSS-REFERENCE TO RELATED APPLICATIONS

This is continuation of U.S. application Ser. No. 14/033,761, now U.S. Pat. No. 8,808,736, filed Sep. 23, 2013, which claims priority to U.S. provisional application 61/815,073, filed Apr. 23, 2013 and U.S. provisional application 61/880,294, filed Sep. 20, 2013; and which is a continuation-in-part of U.S. application Ser. No. 13/367,747, filed Feb. 7, 2012, now U.S. Pat. No. 8,568,776, which claims priority to U.S. provisional Application No. 61/486,523, filed May 16, 2011 and U.S. provisional Application No. 61/441,716, filed Feb. 11, 2011. Each of these prior applications is incorporated by reference in its entirety.

FIELD OF THE INVENTION

The invention relates to enteric coated multiparticulate compositions, and, more particularly, to enteric coated multiparticulate compositions containing peppermint oil.

BACKGROUND

Peppermint oil is used to address gastrointestinal problems because it inhibits the smooth muscles in the gastrointestinal tract from contracting. Unfortunately, however, if peppermint oil is released in the stomach, it is absorbed quickly and can upset the stomach. To overcome this problem, others have developed enteric coated peppermint oil formulations that allow the peppermint oil to pass into the intestines before it is released.

In conventional enteric coated peppermint oil formulations, the peppermint oil is loaded into a hollow capsule that is enteric coated. The enteric coating prevents the capsule from dissolving in the stomach, but allows the capsule to dissolve in the intestines and release the peppermint oil.

Single-unit enteric coated peppermint oil capsules such as these have several drawbacks. First, the dose of peppermint oil that is actually absorbed by the intestines of the person taking the capsule is unpredictable. One of the reasons for this is that, when the capsule dissolves, it quickly dumps all of the peppermint oil into the same area of the intestines, which is problematic because peppermint oil is not very water soluble. Another of the reasons for this is that food in the gastrointestinal tract affects the amount of peppermint oil absorbed.

A second drawback associated with single-unit enteric coated peppermint oil capsules is that the onset of action of the peppermint oil is unreliable. The primary factor delaying the onset of action is the amount of time the capsule spends in the stomach, which ranges over several hours and depends on the amount of food in the stomach. In order to get a reliable onset of action, one should take the capsules on an empty stomach. But because some gastrointestinal disorders flare up after a meal, people often want to treat the flare up immediately. Accordingly, the single-unit enteric coated capsules are not ideal for treating acute gastrointestinal flare ups that are triggered by food.

A third drawback associated with single-unit enteric coated peppermint oil capsules is the fact that peppermint oil is volatile. If the capsules are shipped or stored much above room temperature for extended periods of time, the peppermint oil can evaporate and permeate the capsule.

We surmised that these problems could be addressed by developing enteric coated multiparticulate compositions containing peppermint oil, but found that it is difficult to do so because peppermint oil is very volatile. If multiparticulate cores containing peppermint oil are heated or stored for extended periods, much above room temperature, the volatile components of the peppermint oil leave the cores and permeate the enteric coating. This made it difficult to process the cores, especially when it came time to cure the enteric coating on the cores at elevated temperatures.

In U.S. patent publication 2012/0207842, we described making enteric coated multiparticulate L-menthol compositions. In order to prevent the L-menthol from sublimating as the cores were being processed, we resorted to low temperature processing techniques. The L-menthol multiparticulate compositions described in that application provided the release profile that we desired and worked well for some applications, but were not optimized for all applications.

We have identified a need for a peppermint oil composition that avoids the drawbacks associated with single-unit enteric coated capsules and can be made using conventional room temperature processing techniques

SUMMARY

A multiparticulate composition that embodies these principles comprises a plurality of individual enteric coated cores that include a hydrophobic phase containing peppermint oil dispersed in a microcrystalline cellulose-based gel and a hydrophilic phase containing a hydrogel. The microcrystalline cellulose functions as a release controlling polymer for the peppermint oil, preventing dose dumping and stabilizing the peppermint oil while the cores are being processed.

In another composition aspect of the invention, the multiparticulate composition comprises a plurality of individual enteric coated cores containing about 15% w/w to about 40% w/w peppermint oil, about 35% w/w to about 75% w/w microcrystalline cellulose, and about 2% w/w to about 15% w/w methylcellulose, wherein the % w/w is the % w/w of the enteric coated cores.

In some cases, including a continuous proteinaceous subcoating layer covering the individual cores and separating the individual cores from their respective enteric coatings may be advantageous because the proteinaceous subcoating layer further enhances the stability of the peppermint oil. The continuous proteinaceous subcoating is adapted to prevent the peppermint oil from mixing with the enteric coating.

Some preferred proteinaceous subcoatings have the following attributes: the subcoating may comprise a gelatin film adhered to the core and/or the subcoating may comprise a dried proteinaceous gel.

The enteric coating may have a glass transition temperature higher than a standard boiling point of the peppermint oil.

In a particular embodiment, the enteric coated cores release no more than about 20% of the peppermint oil within about two hours of being placed in a 0.1 N HCl solution and, subsequently, no less than about 85% of the peppermint oil within about eight hours of being placed in a substantially neutral pH environment.

Preferably, the enteric coated cores are spheroidal and not more than 3 mm in diameter.

In a first method aspect of the invention, a method of making a multiparticulate composition comprises blending peppermint oil, microcrystalline cellulose, a hydrogel-forming polymer, and water to form a wet mass including a hydrophobic phase containing the peppermint oil dispersed in a gel formed by the microcrystalline cellulose and a hydrophilic phase containing the hydroxypropyl methylcellulose and water; extruding the wet mass to form an extrudate; dividing the extrudate into individual wet cores; removing water from the hydrophilic phase in the wet cores to form dried cores; and applying an enteric coating to the dried cores.

The method may further comprise coating the dried cores with a liquid proteinaceous material and drying the liquid proteinaceous material to form sub-coated cores prior to applying the enteric coating. The liquid proteinaceous material may comprises gelatin. A particular example of the liquid proteinaceous material is a solution containing at least about 50% gelatin.

The dried cores may be coated with the liquid proteinaceous material by spraying the liquid proteinaceous material onto the dried cores.

Once made, the enteric coated cores are preferably spheroidal and not more than 3 mm in diameter.

Removing water from the hydrophilic phase in the wet cores to form dried cores is preferably achieved without substantially removing peppermint oil.

In a second method aspect of the invention, a method of treating a gastrointestinal disorder in a subject comprises administering to the subject a multiparticulate composition comprising a plurality of individual enteric coated cores that include a hydrophobic phase containing peppermint oil dispersed in a microcrystalline cellulose-based gel and a hydrophilic phase containing a methylcellulose-based gel. Administering is preferably performed enterally. If desired, the multiparticulate composition may be blended with an acidic vehicle prior to being administered.

These and other aspects, embodiments, and advantages of the invention will be better understood by reviewing the accompanying figures and the Detailed Description of Preferred Embodiments.

DETAILED DESCRIPTION OF PREFERRED EMBODIMENTS

Figure 1:
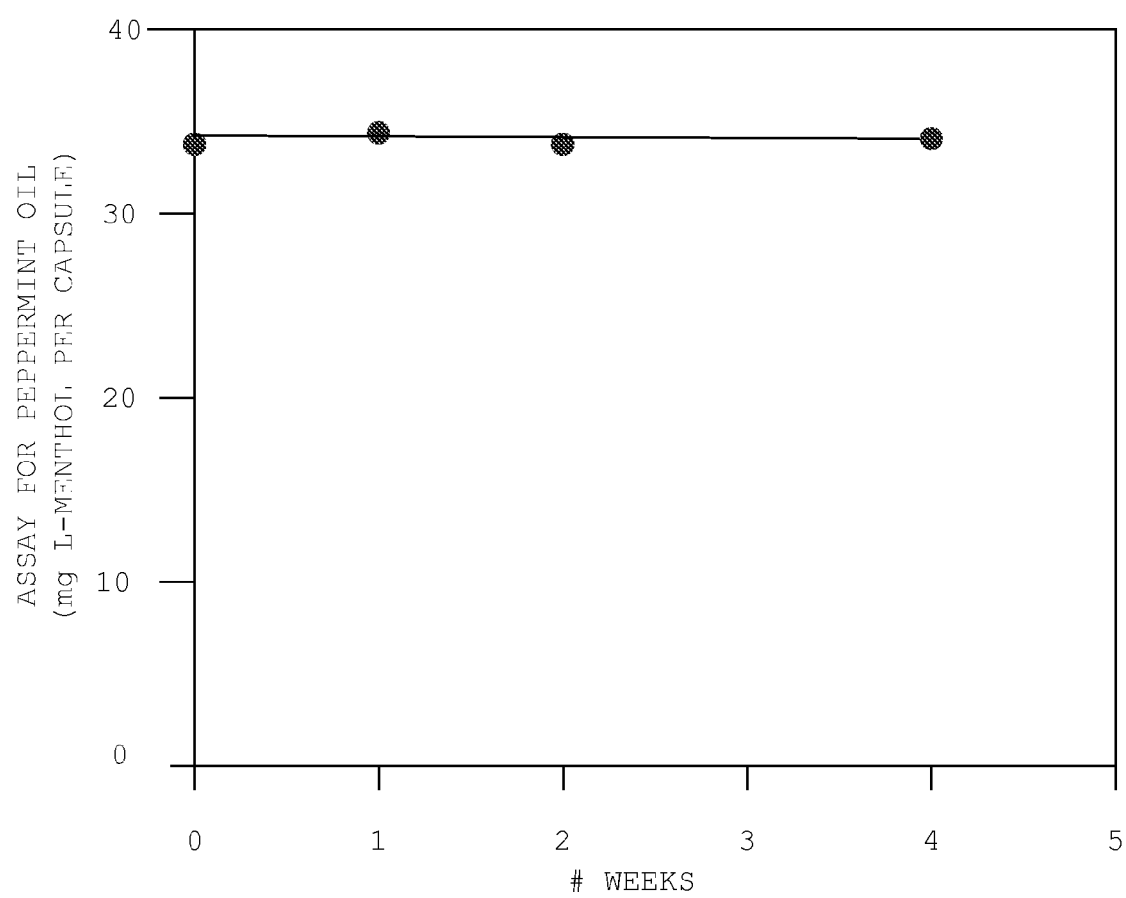
FIG. 1 is a graph showing the results of an accelerated stability assay for a multiparticulate composition according to an embodiment of the invention stored at 40 degrees C. and 75% relative humidity for four weeks.

In the Summary and Detailed Description of Preferred Embodiments reference is made to particular features (including method steps) of the invention. It is to be understood that the disclosure of the invention in this specification includes all possible combinations of such particular features, even if those combinations are not explicitly disclosed together. For example, where a particular feature is disclosed in the context of a particular aspect or embodiment of the invention, that feature can also be used, to the extent possible, in combination with and/or in the context of other particular aspects and embodiments of the invention, and in the invention generally.

The term "comprises" is used herein to mean that other ingredients, steps, etc. are optionally present. When reference is made herein to a method comprising two or more defined steps, the steps can be carried in any order or simultaneously (except where the context excludes that possibility), and the method can include one or more steps which are carried out before any of the defined steps, between two of the defined steps, or after all of the defined steps (except where the context excludes that possibility).

In this section, the invention will be described more fully with reference to its preferred embodiments. The invention may, however, be embodied in many different forms and should not be construed as limited to the embodiments set forth herein. Rather, these embodiments are provided so that this disclosure will convey preferred embodiments of the invention to those skilled in the art.

Because peppermint oil is so volatile, it is difficult to make peppermint oil-containing dosage forms. Conventional processing methods for making pharmaceutical dosage forms involve heating, which conventional wisdom suggests one should avoid when using volatile ingredients. We found that it is very difficult to make stable multiparticulate peppermint oil-containing compositions, for this and other reasons.

Microcrystalline cellulose, or "MCC," is a pharmaceutical excipient that is widely used as a disintegrant in solid oral dosage forms. MCC promotes the breakup of tablets in aqueous environments to enhance drug release. It does this by wicking moisture through the pores of the tablet, weakening the tablet and causing it to disintegrate. Since MCC is used as a disintegrant, its causes the active ingredients in the solid oral dosage form to be released faster than they would otherwise be released.

We found that MCC also functions as a release-controlling polymer for peppermint oil and developed multiparticulate enteric coated peppermint oil compositions using MCC as a release-controlling polymer in the core. The MCC gradually releases the peppermint oil into the intestines rather than quickly dumping the entire dose in a small region of the intestines. Accordingly, the MCC in our multiparticulate peppermint oil compositions performs the opposite function of a disintegrant and overcomes the dose-dumping drawback held by the conventional single-unit enteric coated capsules.

The multiparticulate composition aspect of the inventions is first described. The multiparticulate composition is adapted to carry peppermint oil to the intestines and includes a plurality of particulates that are preferably spheroidal in shape and are sized to fit through the pyloric sphincter when it is in a relaxed state. The diameter of each particulate is preferably in the range of about 0.1 mm to about 3 mm or, about 1 mm to about 2.5 mm, or less than about 1.4 mm. Particulates of this diameter are advantageous because they can fit through the pyloric sphincter and do not remain in the stomach as long as single-unit capsules, thereby providing a more reliable onset of action.

The multiparticulate composition includes a plurality of individual peppermint-oil containing cores that are each enteric coated. The enteric coating allows the individual cores to pass through the stomach without releasing a substantial amount of peppermint oil. In the pH of the intestines, the enteric coating dissolves, exposing the cores and allowing peppermint oil to be released.

The core contains the primary active ingredient peppermint oil, but may also contain other secondary active ingredients such as one or more other terpene-based substances such as terpenes, terpenoids, and/or essential oils. Terpene-based substances that may be used as secondary active ingredients include but are not limited to L-menthol, caraway oil, orange oil, ginger oil, turmeric oil, curcumin oil, and fennel oil, among others.

Alternatively, the secondary active ingredient may be a non-terpene-based substance that helps relieve gastrointestinal disorder symptoms from their various actions. Examples of non-terpene secondary active ingredients include, but are not limited to, polyphenols such as green tea extracts and aloe vera powder, proton pump inhibitors, anti-inflammatories, and immune suppressors among others.

Essential oils such as peppermint oil, caraway oil, orange oil, fennel oil, etc. are liquid at room temperature. They are usually formulated as liquids in a capsule, with an enteric-coating over the capsule. We discovered that essential oils can be mixed with a cellulosic filler and a binder to make a dough or wet mass, but the dough formed by simply mixing these materials together does not produce a core with the desired strength for subcoating and further processing. By adding water to the wet mass, we produced cores containing peppermint oil that were robust enough for subsequent processing.

The core may also contain one or more antioxidants that can maintain the purity of the peppermint oil and other active ingredients if used. This is useful because peppermint oil can oxidize to form undesirable derivatives. Examples of antioxidants that may be used include, but are not limited to tocopherol (vitamin E,) BHT (butylated hydroxy toluene), BHA (butylayted hydroxy anisole), and ascorbic acid.

In the core, peppermint oil is combined with MCC and a hydrogel forming polymer binder such as s a cellulose-based, starch-based, and/or povidone-based binder. It is to be understood that "cellulose-based," "starch-based" binders, and "povidone-based" binders includes cellulose, starch, and povidone derivatives. When mixed with water, the binder swells to form a hydrogel matrix. In contrast, MCC and peppermint oil are hydrophobic. Examples of cellulose-based binders include methylcellulose based polymers, including, for example, methylcellulose and hydroxypropyl methylcellulose. Methylcellulose is particularly preferred for use in the composition.

When water is added to the core during processing, these materials separate into a hydrophobic phase and hydrophilic phase. The hydrophobic phase contains peppermint oil dispersed in the microcrystalline cellulose-based gel and the hydrophilic phase contains the hydrogel. The peppermint oil is therefore, dispersed throughout the hydrophobic phase, which is in contact with the hydrophilic phase.

One of the advantageous of dispersing the peppermint oil in MCC is that it allows excess water to be removed from the cores without also removing a substantial amount of the peppermint oil. Conventional drying techniques would cause the peppermint oil in the core to evaporate with the water. Thus, by making the core to include a hydrophobic phase containing peppermint oil dispersed in a microcrystalline cellulose-based gel and a hydrophilic phase containing a methylcellulose-based polymer, the core can be processed without risking substantial loss of the peppermint oil.

The core may also include pharmaceutically acceptable fillers, stabilizers, binders, surfactants, processing aids, and/or disintegrants. By way of example only, suitable materials for performing these functions are provided.

Preferred fillers include cellulosic filler materials such as microcrystalline cellulose, dibasic calcium phosphate, and/or another pharmaceutically acceptable filler.

Preferred binders include cellulosic water soluble polymers such as methylcellulose, starch, hydroxypropyl cellulose, gelatin, polyvinylpyrrolidone, polyethylene glycol, and/or another pharmaceutically acceptable binder.

In some cases, it may be advantageous to include a surfactant as a solubilizing agent. If used, preferred solubulizing agents include but are not limited to polysorbate 80 and/or sodium lauryl sulfate. Advantageously when polysorbate 80 is used, it may also enhance absorption of terpene-based active ingredients into the plasma.

Suitable processing aids include pharmaceutically acceptable processing aids for improving the flowability of the core materials during processing. Preferred processing aids include, but are not limited to, colloidal silicon dioxide, talc, magnesium stearate, stearin, and/or another pharmaceutically acceptable processing aid.

Preferred disintegrants include, but are not limited to, croscarmellose sodium, polyvinylpyrrolidone (crospovidone) sodium starch glycolate, and/or another pharmaceutically acceptable processing aid.

In a particularly preferred embodiment of the multiparticulate composition, the cores contain about 15% w/w to about 40% w/w peppermint oil, about 35% w/w to about 75% w/w microcrystalline cellulose, and about 2% w/w to about 15% w/w methylcellulose, wherein the % w/w is the % w/w of the enteric coated cores.

Because it is often desirable to be able to ship products in non-refrigerated vehicles and store them for a long period of time, we preferred for our peppermint oil-containing multiparticulate composition to be stable when stored at 40 degrees C. and 75% relative humidity, from between 1 day to 30 days, and even longer. This would also be useful if the multiparticulate composition is distributed in regions in climate zone IV.

While developing multiparticulate compositions containing terpene-based active ingredients, however, we found that volatile ingredients sometimes penetrated the conventional subcoating materials we used to separate the cores form their enteric coatings. Because of this, the active ingredients would come in contact with the enteric coating if the temperature was elevated (25 degrees C.-50 degrees C.) or the composition was stored for a long period of time. This somewhat reduced the effectiveness of the enteric coating and amount of active ingredient in the core.

We solved this problem by developing a new subcoating material that may be applied to the finished core and prevents volatile active ingredients in the core from leaving the core and permeating the enteric coating at elevated temperatures. The subcoating includes a proteinaceous material that is applied along each core's exterior surface to form a substantially continuous thin film that forms a barrier between the core and the enteric coating that is applied after the subcoating.

Examples of proteinaceous materials that may be used in the subcoating include proteins such as, but not limited to casein, whey protein, soy protein, and various types of gelatin (Type A, Type B or derivatives of gelatin) or proteinaceous materials that have protein-like structures. A particularly preferred material used to form the subcoating is a solution containing at least about 50% of the proteinaceous material dispersed in a solvent. The solvent is preferably, but not necessarily water. A particularly preferred proteinaceous material is Type A gelatin.

The proteinaceous subcoating is preferably applied to the core in liquid form and subsequently dried on the core. When dry, the subcoating adheres to the core. Examples of the liquid form of the proteinaceous subcoating material include melts and gels. When dry, the subcoating forms a continuous film over the core and provides a barrier between the core and enteric coating.

Gelatin typically melts at about 35 degrees C., which is below the normal human body temperature of about 37 degrees C. Given this, one might expect that, if a multiparticulate composition, including a gelatin subcoating, is heated above 35 degrees C., the subcoating will melt and release the active ingredients from the core. We observed, however, that gelatin subcoated multiparticulate compositions did not release the terpene-based active ingredients from the core even when heated above 35 degrees C. This is a particularly unexpected result that provides numerous advantages.

Because the proteinaceous subcoating prevents volatile peppermint oil from being released from the core even when heating above the melting point of the proteinaceous material, by applying the proteinaceous subcoating, one does not have to avoid heating the subcoated cores during processing. One scenario in which this is advantageous is when the enteric coating is applied. Enteric coating polymers have a glass transition temperature ($T_g$) that is often above 35 degrees C. After being applied to a core, enteric coated particulates are preferably heated above $T_g$ so that the enteric coating polymer can cure, thereby achieving optimum enteric protection of the core. Thus, using the proteinaceous subcoating between the core and enteric coating allows one to achieve optimum enteric protection without releasing the peppermint oil from the core.

The subcoating may be applied to the core as a gelatin-containing subcoating solution. The solvent may be any solvent in which gelatin is soluble, such as water. In a preferred embodiment, the subcoating solution comprises about 5% to about 30% w/w gelatin and about 70% to about 95% solvent. When the subcoating solution is allowed to dry around the core, the solvent evaporates, leaving a thin gelatin film that adheres to the core and forms a barrier between the core and enteric coating. The gelatin film subcoating is preferably about 3.5% w/w to about 35% w/w of the enteric coated particulates. Surprisingly, in our experiments, drying the cores containing peppermint oil and water, at about 15 degrees C. to about 25 degrees C. did not result in significant loss of the peppermint oil as the water was being removed by fluid bed drying.

The enteric coating is applied over each core, or, if a subcoating is used, over the subcoating. In a preferred embodiment, the enteric coating is about 2% w/w to about 35% w/w of the enteric coated particulate. A preferred enteric coating material is a methacrylic acid based material such as a methacrylic acid based co-polymer. These materials may be combined with other materials such as plasticizers for forming an enteric coating solution. In a typical embodiment, the enteric coating solution comprises about 5% w/w to about 35% w/w water, and the enteric-coated dried multiparticulates contain 0.5% w/w to about 5% w/w plasticizer, about 0.05% w/w to about 5% w/w anti-adherent, and about 2% w/w to about 35% w/w methacrylic acid copolymer. By way of example only, a suitable plasticizer is triethyl citrate and a suitable anti-adherent is PLASACRYL T20 (Emerson Resources, Inc., Norristown, Pa.). The enteric coating is preferably about 3.5% w/w to about 35% w/w of the enteric coated particulates.

The enteric-coated particulates may be coated with a finish coat. The finish coat is used, for example, to overcome the mucoadhesive properties of some enteric coating materials, which make the multiparticulates stick together during processing, storage, or dispensing through a tube for enteral feeding. The finish coat is preferably a cellulosic derivative such as HPMC (hydroxylpropyl methylcellulose), HPC (hydroxyl propyl cellulose), CMC (carboxy methylcellulose), or another pharmaceutically acceptable finish coating material. When used, the finish coat is preferably about 1% to 10% w/w of the finished multiparticulate.

A particularly preferred finish coat material is HPMC because is not mucoadhesive. As such, it prevents the multiparticulates from sticking to the stomach wall as well as food in the stomach. This allows the multiparticulates to reach the intestines quickly, making the onset of action more reliable than the single-unit capsules.

The release profile of peppermint oil in the body can be varied to treat different disorders. Peppermint oil can be used to treat a plethora of gastrointestinal disorders such as irritable bowel syndrome, inflammatory bowel disease, gastroparesis, and functional dyspepsia, but it is best to release the active ingredients at a certain point in the gastrointestinal tract to optimally treat each disorder.

To treat gastrointestinal disorders associated with irritable bowel syndrome, the multiparticulate composition is formulated to minimize the amount of peppermint oil released into the stomach and colon, so that most of it is released in the small intestine. Preferably, 20% or less of the peppermint oil is released into the stomach and 20% or less of the peppermint oil is released into the colon. Also, in many instances such as IBS, the peppermint oil is preferably gradually released over the course of about 4 to about 8 hours after the multiparticulates pass the pyloric sphincter into the small intestine in order to deliver the active ingredients locally in the small intestine. This release profile treats gastrointestinal disorders by stabilizing the digestive system and alleviating the symptoms associated with disorders such as irritable bowel syndrome.

To treat a gastrointestinal disorder such as functional dyspepsia (classified as a gastro-duodenal disorder), the multiparticulate composition is formulated so that the peppermint oil is rapidly released after the multiparticulates pass through the stomach and the pylorus, over the course of about 0 to about 2 hours in order to deliver peppermint oil locally to the duodenum section of the small intestine to help stabilize the digestive system and/or alleviate the symptoms associated with functional dyspepsia. Preferably, 20% or less of the peppermint oil is released in the stomach and 20% or less of the peppermint oil is released in the jejunum and ileum sections of the small intestine (which follow the duodenum) and the colon.

To treat a gastrointestinal disorder such as inflammatory bowel disease, including ulcerative colitis or Crohn's disease), the multiparticulate composition is formulated so that the peppermint oil is rapidly released after the multiparticulates pass through the stomach and the small intestine, over the course of about 4 to about 6 hours, in order to deliver the peppermint oil locally to the colon to attenuate the inflammatory response and/or alleviate the symptoms associated with inflammatory bowel disease. Preferably, 30% or less of the peppermint oil is released in the stomach and small intestine and greater than 70% of the peppermint oil is released in the first 2 hours after the multiparticulates reach the pH of the colon.

In a particularly preferred embodiment, the enteric coated cores of the multiparticulate composition release no more than about 20% of the peppermint oil within about two hours of being placed in a 0.1 N HCl solution and, subsequently, no less than about 85% of the peppermint oil within about eight hours of being placed in a substantially neutral pH environment.

It should be understood that where this disclosure makes reference to treating a gastrointestinal disorder, that the terms "treat," "treating, or any other variation of the word "treat," include prevention of the gastrointestinal disorder.

The core formulation allows one to achieve a suitable release profile because the MCC acts as a release controlling polymer for peppermint oil. One skilled in the art will recognize that that the release rate of peppermint oil from the core can be adjusted by including a disintegrant, that actually functions as a disintegrant, or another conventional release controlling polymer.

A daily dose of a multiparticulate composition containing peppermint oil is about 20 mg to about 1200 mgs of peppermint oil, split into 2 or three doses per day. Each dosage form may contain between 10 mgs and 140 mgs of peppermint oil, more preferably, about 90-110 mg of peppermint oil.

Doses of the multiparticulate composition may be administered sporadically when needed for treating acute inflammations of the gastrointestinal tract or may be administered as part of a long term regimen for treating GI disorders such as irritable bowel syndrome, functional dyspepsia, gastroparesis, or inflammatory bowel disease. A treatment subject may be a human or animal.

The enteric coated multiparticulates may be prepared into a suitable pharmaceutical or medical food dosage form such as a capsule, tablet or sachet, or are mixed with an acidic food vehicle and directly fed through a feeding tube. A typical dosage form contains about 400 mg of the particulates, but, depending on the desired dosage, this amount may be adjusted. Acidic food vehicles include citrus juices and foods such as, for example, apple sauce and apple juice.

The multiparticulate composition is preferably formulated to be administered enterally, such as orally or through a feeding tube, to a human or animal subject to ensure that the subject receives an effective amount of peppermint oil over the course of several hours after ingestion. The feeding tube may help with subjects that have achalasia, dysphagia, or another disorder that does not allow them to administer a capsule orally with water. Alternatively the multiparticulates can be sprinkled onto apple sauce for patients that cannot swallow larger sized capsules.

A preferred method of making the multiparticulate composition is now described. The core is typically prepared by wet granulating the core materials into a wet mass, extruding the wet mass to form an extrudate, cutting the extrudate into a plurality of core pieces, and spheronizing the core pieces. The spheronized core pieces are then dried in a dryer such as a fluid bed dryer to remove the water. If desired the dried spheronized cores are then sieved to separate cores of different sizes.

The dried spheronized cores are then coated with the proteinaceous subcoating material if desired. One way to apply the subcoating material to the cores is to prepare a subcoating solution and spray the subcoating solution onto the cores. There are various conventional methods for doing this, but the preferred method is Wurster coating or fluid bed coating (top spray or bottom spray). The subcoating solution is subsequently allowed to dry over the cores, leaving each core coated with a thin, continuous proteinaceous film. If desired, the subcoated cores are sieved to separate them into different sizes.

The enteric coating is then applied to the subcoated cores or directly to the cores if no subcoating is used. One means of applying the enteric coating is to spray it onto the subcoated cores. There are various conventional methods for doing this, but the preferred method is Wurster coating or fluid bed coating. The enteric coated particulates are subsequently dried. During the enteric coating process, the cores are preferably heated in an environment that is about 20 degrees C. to about 50 degrees C. to cure the enteric coating materials above their $T_g$.

A finish coating may be applied over the enteric coated particulates if desired. One way to apply the finish coating is to spray it onto the enteric coated cores. There are various conventional methods for doing this, but the preferred method is Wurster coating or fluid bed coating.

A more particular method of making a multiparticulate composition involves blending the peppermint oil, microcrystalline cellulose, hydrogel-forming polymer, and water to form the wet mass. The wet mass includes a hydrophobic phase containing the peppermint oil dispersed in a gel formed by the microcrystalline cellulose and a hydrophilic phase containing the hydrogel and water. The wet mass is extruded then extruded to form an extrudate and the extrudates is divided into individual wet cores. Water is removed from the hydrophilic phase in the wet cores to form dried cores. The enteric coating is then applied to the dried cores.

Another method aspect of the invention is a method of treating a gastrointestinal disorder. This method comprises administering to the subject a multiparticulate composition comprising a plurality of individual cores including a hydrophobic phase containing peppermint oil dispersed in a microcrystalline cellulose-based gel and a hydrophilic phase containing methylcellulose and an enteric coating over the individual cores.

The multiparticulate composition can be enterally administered through use of a conventional oral dosage form such as a tablet, caplet, capsule, or sachet, among others.

Another enteral means for administering the multiparticulate composition, either orally or via a tube, is by adding it to food. In this instance, the multiparticulate composition is blended with an acidic food vehicle such as apple juice or another acidic vehicle that prevents premature release of the active ingredients and is then ingested by the subject.

EXAMPLES

This section provides specific examples of the multiparticulate composition and method aspects of the invention. These examples are provided to illuminate certain preferred aspects and embodiments of the invention, but the scope of the invention is not limited to what these examples teach.

Example 1

Preparation of a Multiparticulate Composition

The core was prepared using microcrystalline cellulose (MCC) commercially available under the name AVICEL PH 102 (FMC Corp., Philadelphia, Pa.), methylcellulose commercially available under the name METHOCEL A15LV (Dow Chemical Co., Midland, Mich.), distilled peppermint oil, and USP purified water.

33.25 kg MCC, 1.75 kg methylcellulose, and 15 kg peppermint oil were blended with water to form a wet mass. The wet mass was granulated in a high shear granulator. The granulated wet mass was then extruded and spheronized. The spheronized particles were subsequently dried in a fluid bed dryer to form uncoated cores. The drying temperature was about 16 degrees C.

The uncoated cores were Wurster coated with 37 kg of a subcoating composition containing about 15% acid bone gelatin and 85% USP water and dried.

The subcoated cores were Wurster coated with 31 kg of a 20% w/w enteric coating suspension containing KOLLICOAT MAE 30 DP, PLASACRYL T20, triethyl citrate USP, and purified water USP. The dry solids weight of amount KOLLICOAT MAE 30 DP was approximately 5.4 kg. The dry solids weight of triethyl citrate was approximately 0.28 kg. The dry solids weight of PlasACRYL® T20 was approximately 0.5 kg. The enteric coated cores were then dried at about 40 degrees C. KOLLICOAT MAE 30 DP is a methacrylic acid/ethyl acrylate co-polymer. PLASACRYL T20 is an emulsion of anti-tacking agent and plasticizer and contains water, glyceryl monostearate, triethyl citrate and polysorbate 80.

The enteric coated cores were Wurster coated with 26 kg of a finish coat solution containing about 10% w/w hydroxyl propyl methyl cellulose and 90% water USP and dried at about 40 degrees C.

Example 2

Stability Testing of the Multiparticulate Composition of Example 1

The multiparticulate composition described in Example 1 was subsequently tested to ensure that the gelatin subcoating prevented the peppermint oil from evaporating and leaving the core when stored at elevated temperatures over a long period of time.

In the first set of experiments, we prepared capsules containing the multiparticulate composition and stored them at degrees C. and 75% relative humidity for four weeks. Each week, we measured the amount of peppermint oil in a selection of the capsules. FIG. 1 shows the results of this study as a graph of the number of milligrams of L-menthol per capsule as a function of time. The results show that the amount of L-menthol in the capsules remained more or less constant at about 34 mg during the four week period. This proves that the gelatin subcoating maintains the integrity of the core.

In the second set of experiments, we simulated the gastrointestinal environment and measured the dissolution profile of the multiparticulate composition to ensure that the enteric coating worked and that almost all of the peppermint oil would be released from the core within about 8.5 hours. This was a conventional two stage dissolution study in which the sample was placed in an acidic medium (0.1 N HCl) for about two hours and subsequently placed in a neutral medium (pH=6.8) for the remainder of the time.

Figure 2:
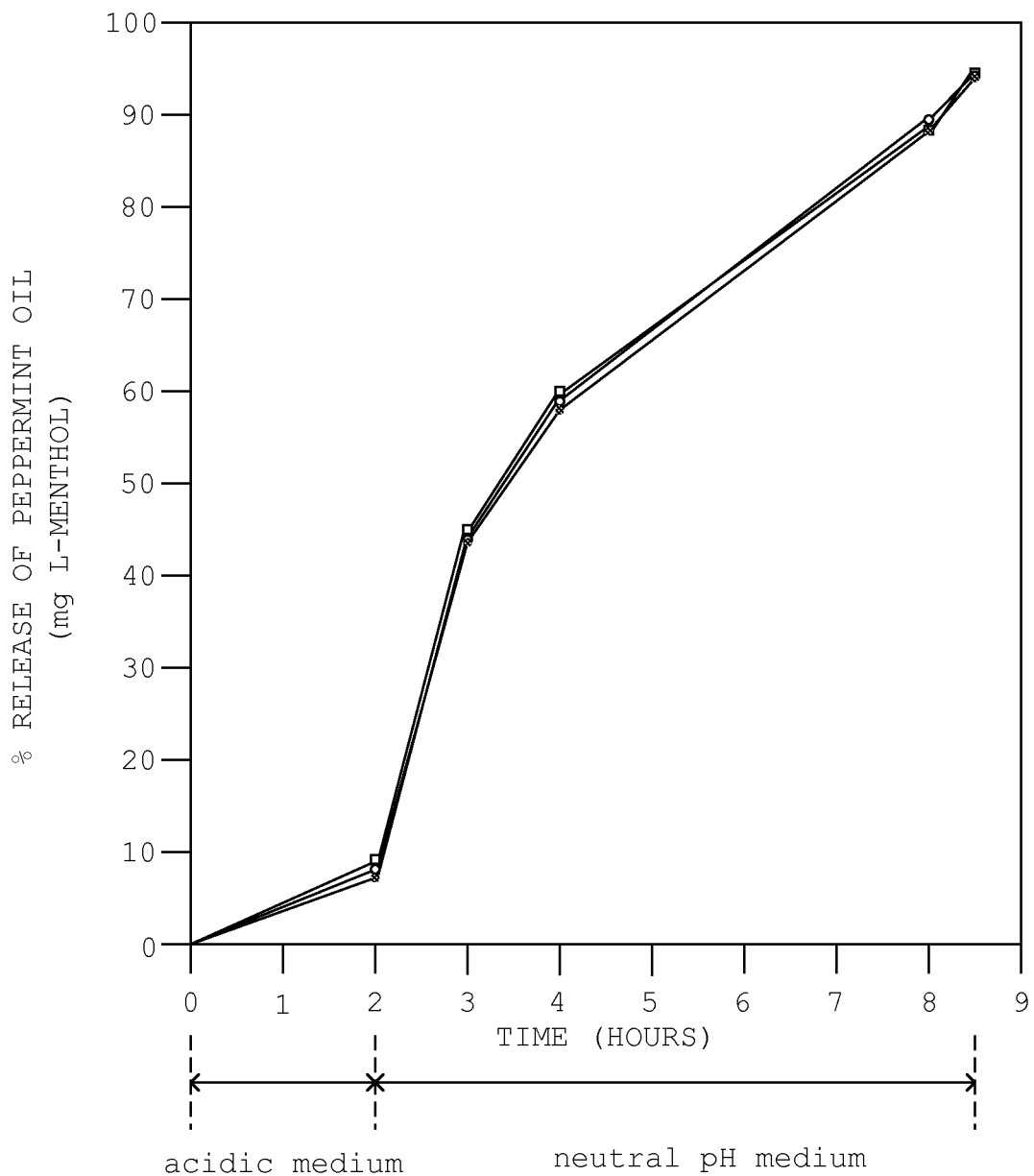
FIG. 2 is a graph showing the results of a two-stage dissolution test for a multiparticulate composition according to an embodiment of the invention after the composition was stored at 40 degrees C. and 75% relative humidity.

The results of this experiment are shown in FIG. 2 as the % release of peppermint oil, reported as the number of mgs of L-menthol over time. After two hours in the acidic medium, each of the samples tested had only released about 10% or less of the peppermint oil, indicating that the enteric coating was intact and worked normally. Over the following 6.5 hours in the neutral medium, the peppermint oil was gradually released from the core.

Unless otherwise defined, all technical and scientific terms used herein are intended to have the same meaning as commonly understood in the art to which this invention pertains and at the time of its filing. Although various methods and materials similar or equivalent to those described herein can be used in the practice or testing of the present invention, suitable methods and materials are described. The skilled should understand that the methods and materials used and described are examples and may not be the only ones suitable for use in the invention.

The specification discloses typical preferred embodiments of the invention, and although specific terms are employed, the terms are used in a descriptive sense only and not for purposes of limitation. The invention has been described in some detail, but it will be apparent that various modifications and changes can be made within the spirit and scope of the invention as described in the foregoing specification and in the claims.

That which is claimed is:

1. A composition providing controlled-release of peppermint oil, the composition comprising a plurality of enteric coated solid spheroidal cores, the cores comprising peppermint oil, microcrystalline cellulose, and a hydrophilic binder, the cores having a diameter of about 0.1 to about 3 mm.

2. The composition of claim 1, wherein the cores are spheroidal and have a diameter of about 1 mm to about 2.5 mm.

3. The composition of claim 1, wherein the cores are spheroidal and have a diameter of less than about 1.4 mm.

4. The composition of claim 1, wherein the cores release no more than about 20% of the peppermint oil within about two hours of being placed in a 0.1 N HCl solution and, subsequently no less than about 85% of the peppermint oil within about eight hours of being placed in a substantially neutral pH environment.

5. The composition of claim 1, wherein the cores release no more than about 20% of the peppermint oil within about two hours of being placed in a 0.1 N HCl solution and, subsequently no less than about 60% of the peppermint oil within about two hours of being placed in a substantially neutral pH environment.

6. The composition of claim 1, wherein the peppermint oil in the cores is present in combination with at least one terpene-based substance selected from L-menthol, caraway oil, orange oil, ginger oil, turmeric oil, curcumin, and fennel oil.

7. The composition of claim 1, wherein the peppermint oil in the cores includes L-menthol and the peppermint oil is present in combination with more L-menthol than provided by the peppermint oil itself.

8. The composition of claim 1, wherein the peppermint oil in the cores is present in combination with caraway oil.

9. The composition of claim 1, wherein the cores further comprise a continuous proteinaceous subcoating layer positioned between the solid core and enteric coating.

10. The composition of claim 9, wherein the proteinaceous subcoating layer comprises a gelatin film adhered to the solid core.

11. The composition of claim 9, wherein the proteinaceous subcoating layer comprises a dried proteinaceous gel.

12. The composition of claim 1, wherein the hydrophilic binder is methylcellulose.

13. The composition of claim 1, wherein the hydrophilic binder is selected from starch-based, cellulose-based, and povidone-based materials.

14. The composition of claim 1, wherein the cores comprise about 15% w/w to about 40% w/w peppermint oil, about 35% w/w to about 75% w/w microcrystalline cellulose, and about 2% w/w to about 15% w/w methylcellulose.

15. The composition of claim 1, wherein the enteric coating comprises a methacrylic acid-based co-polymer.

16. The composition of claim 1, wherein the cores further comprise at least one disintegrant selected from croscarmellose sodium, polyvinylpyrrolidone, and sodium starch glycolate.

17. An oral controlled-release multiparticulate dosage form comprising a plurality of individually enteric coated peppermint oil containing particulates that independently disperse in a subject's stomach after oral ingestion and travel through the stomach without substantially releasing the peppermint oil therein, the individual particulates comprising (a) a solid core containing peppermint oil, microcrystalline cellulose, and a hydrophilic binder; and (b) an enteric coat over the core.

18. The dosage form of claim 17, wherein the individual particulates are spheroidal and have a diameter of about 0.1 mm to about 3 mm.

19. The dosage form of claim 18, wherein the diameter is about 1 mm to about 2.5 mm.

20. The dosage form of claim 18, wherein the diameter is about 1 mm to about 1.4 mm.

21. The dosage form of claim 17, wherein the individual particulates release no more than about 20% of the peppermint oil within about two hours of being placed in a 0.1 N HCl solution and, subsequently no less than about 85% of the peppermint oil within about eight hours of being placed in a substantially neutral pH environment.

22. The dosage form of claim 17, wherein the individual particulates release no more than about 20% of the peppermint oil within about two hours of being placed in a 0.1 N HCl solution and, subsequently no less than about 60% of the peppermint oil within about two hours of being placed in a substantially neutral pH environment.

23. The dosage form of claim 17, wherein the peppermint oil in the individual particulates is present in combination with at least one terpene-based substance selected from L-menthol, caraway oil, orange oil, ginger oil, turmeric oil, curcumin, and fennel oil.

24. The dosage form of claim 17, wherein the peppermint oil in the individual particulates includes L-menthol and the peppermint oil is present in combination with more L-menthol than provided by the peppermint oil itself.

25. The dosage form of claim 17, wherein the peppermint oil in the individual particulates is present in combination with caraway oil.

26. The dosage form of claim 17, wherein the individual particulates further comprise a continuous proteinaceous subcoating layer positioned between the core and enteric coating.

27. The dosage form of claim 26, wherein the proteinaceous subcoating layer comprises a gelatin film adhered to the solid core.

28. The dosage form of claim 26, wherein the proteinaceous subcoating layer comprises a dried proteinaceous gel.

29. The dosage form of claim 17, wherein the hydrophilic binder is methylcellulose.

30. The dosage form of claim 17, wherein the hydrophilic binder is selected from starch-based, cellulose-based, and povidone-based materials.

31. The dosage form of claim 17, wherein the cores comprise about 15% w/w to about 40% w/w peppermint oil, about 35% w/w to about 75% w/w microcrystalline cellulose, and about 2% w/w to about 15% w/w methylcellulose.

32. The dosage form of claim 17, wherein the enteric coating comprises a methacrylic acid-based co-polymer.

33. The dosage form of claim 17, wherein the cores further comprise at least one disintegrant selected from croscarmellose sodium, polyvinylpyrrolidone, and sodium starch glycolate.

* * * * *